(12) United States Patent
Dias et al.

(10) Patent No.: US 10,077,226 B2
(45) Date of Patent: Sep. 18, 2018

(54) PROCESS FOR PRODUCTION OF ADIPIC ACID FROM 1,6-HEXANEDIOL

(71) Applicant: Archer-Daniels-Midland Company, Decatur, IL (US)

(72) Inventors: Eric L. Dias, Belmont, CA (US); Vincent J. Murphy, San Jose, CA (US); James A. W. Shoemaker, Gilroy, CA (US)

(73) Assignee: Archer-Daniels-Midland Company, Decatur, IL (US)

( * ) Notice: Subject to any disclaimer, the term of this patent is extended or adjusted under 35 U.S.C. 154(b) by 0 days.

(21) Appl. No.: 15/295,351

(22) Filed: Oct. 17, 2016

(65) Prior Publication Data

US 2017/0226038 A1    Aug. 10, 2017

Related U.S. Application Data

(60) Continuation of application No. 14/691,356, filed on Apr. 20, 2015, now abandoned, which is a division of application No. 13/915,120, filed on Jun. 11, 2013, now Pat. No. 9,035,094.

(60) Provisional application No. 61/658,364, filed on Jun. 11, 2012.

(51) Int. Cl.
| | |
|---|---|
| *C07C 55/00* | (2006.01) |
| *C07C 51/235* | (2006.01) |
| *B01J 23/42* | (2006.01) |
| *B01J 21/06* | (2006.01) |
| *B01J 23/652* | (2006.01) |
| *B01J 35/10* | (2006.01) |

(52) U.S. Cl.
CPC .......... *C07C 51/235* (2013.01); *B01J 21/066* (2013.01); *B01J 23/42* (2013.01); *B01J 23/6527* (2013.01); *B01J 35/1014* (2013.01); *B01J 35/1019* (2013.01); *B01J 35/1061* (2013.01); *B01J 35/1066* (2013.01)

(58) Field of Classification Search
CPC ....... C07C 51/235; B01J 23/42; B01J 21/066; B01J 35/1066; B01J 35/1014; B01J 35/1019; B01J 35/1061; B01J 23/6527
See application file for complete search history.

(56) References Cited

U.S. PATENT DOCUMENTS

| | | | |
|---|---|---|---|
| 3,739,020 A * | 6/1973 | McClain et al. ...... | C07C 51/235 560/239 |
| 4,400,468 A | 8/1983 | Faber | |
| 7,119,225 B1 | 10/2006 | Herron et al. | |
| 9,035,094 B2 | 5/2015 | Dias et al. | |
| 2011/0306790 A1 | 12/2011 | Murphy et al. | |

FOREIGN PATENT DOCUMENTS

| | | | |
|---|---|---|---|
| DE | 2407146 | * | 9/1975 |
| DE | 2407146 A1 | | 9/1975 |
| EP | 0585065 A1 | | 3/1994 |
| EP | 1224969 A1 | | 7/2002 |
| JP | 2005-330225 | * | 12/2005 |
| JP | 2005-330225 A | | 12/2005 |
| JP | 2007-520364 A | | 7/2007 |
| WO | 2011/155964 A1 | | 12/2011 |
| WO | 2012/018739 A1 | | 2/2012 |

OTHER PUBLICATIONS

JP2005-330225 translated, 2005.*
DE2407146 description translated 1975.*
DE2407146 claims translated 1975.*
International Search Report and Written Opinion received for PCT Patent Application No. PCT/US2013/045096, dated Jan. 24, 2014, 17 pages.
Prati et al., "Effect of Gold Addition on Pt and Pd Catalysts in Liquid Phase Oxidations", Topics in Catalysis, vol. 44, Nos. 1-2, Jun. 2007, pp. 319-324.
Svetlakov et al., "Oxidation with Nitric Acid of Aliphatic Alcohols and Diols to Carboxylic Acids", Russian Journal of Organic Chemistry, vol. 43, No. 5, 2007, pp. 773-774.

* cited by examiner

*Primary Examiner* — Yevgeny Valenrod
*Assistant Examiner* — Blaine G Doletski
(74) *Attorney, Agent, or Firm* — Senniger Powers LLP

(57) ABSTRACT

Processes are disclosed for the conversion of 1,6-hexanediol to adipic acid employing a chemocatalytic reaction in which 1,6-hexanediol is reacted with oxygen in the presence of particular heterogeneous catalysts including at least one of platinum or gold. The metals are preferably provided on a support selected from the group of titania, stabilized titania, zirconia, stabilized zirconia, silica or mixtures thereof, most preferably zirconia stabilized with tungsten. The reaction with oxygen is carried out at a temperature from about 100° C. to about 300° C. and at a partial pressure of oxygen from about 50 psig to about 2000 psig.

22 Claims, No Drawings

PROCESS FOR PRODUCTION OF ADIPIC ACID FROM 1,6-HEXANEDIOL

CROSS-REFERENCE TO RELATED APPLICATION

This application is a continuation of U.S. application Ser. No. 14/691,356, filed Apr. 20, 2015, now abandoned, which is a divisional of U.S. application Ser. No. 13/915,120, filed Jun. 11, 2013, now issued as U.S. Pat. No. 9,035,094, which claims the benefit under 35 U.S.C. 119(e) of U.S. Provisional Application No. 61/658,364, filed on Jun. 11, 2012, the disclosures of each of which are hereby incorporated by reference in their entirety.

FIELD

The present disclosure relates generally to processes for the chemocatalytic conversion of 1,6-hexanediol to adipic acid. More specifically, the present disclosure relates to processes that involve the use of heterogeneous catalysis in the presence of oxygen, and to new heterogeneous catalysts.

BACKGROUND

Overwhelmingly, commodity, intermediate and specialty organic chemicals used throughout the world are derived, ultimately, from crude oil by processes involving chemical catalysis. Crude oil is first refined, typically by catalyzed steam cracking, into hydrocarbon intermediates such as ethylene, propylene, butadiene, benzene, and cyclohexane. These hydrocarbon intermediates then typically undergo one or more catalytic reactions by various processes to produce the desired chemical(s).

Among the plethora of intermediate and specialty chemicals derived from crude oil is adipic acid. Adipic acid is an important industrial chemical, the primary use of which is as a monomer in the production of nylon 6,6. Other significant uses of adipic acid include use in the production of urethanes, diesters and polyesters. Simplistically viewed, current commercial scale production of adipic acid involves refining crude oil to produce cyclohexane, followed by the selective catalytic oxidization of cyclohexane into "KA oil" which, in turn, is further oxidized in the presence of nitric acid to produce adipic acid.

1,6-Hexanediol is a valuable, specialty chemical. It is currently used in the synthesis of a variety of polymers and other specialty products such as, for example, urethane foams, elastomers, coatings, adhesives and plasticizers. 1,6-Hexanediol is produced industrially by the catalytic hydrogenation of adipic acid or its esters. Mixtures of adipic acid, hydroxycarboxylic acids with other C6 components formed in, for example, the above-mentioned cyclohexane oxidation process can also be used. Typically, adipic acid or such mixtures are hydrogenated continuously in the presence of catalysts comprising cobalt, copper or manganese. Hydrogenation processing conditions include reaction temperatures in the range of about 170-240° C. and pressures in the range of about 15.0-30.0 MPa. These hydrogenation reactions have been conducted in trickle-flow (down-flow) or bubble-flow (up-flow) fixed-bed reactors. The crude reaction product from this hydrogenation reaction typically includes not only 1,6-hexanediol but also other alcohols, ethers, other diols, and esters. The 1,6-hexanediol is typically recovered by fractional distillation of the crude reaction product. If esters of adipic acid are employed as the substrate to produce 1,6-hexanediol, supported catalysts such as copper chromite or copper with added zinc and barium have been used. Ruthenium, platinum, or palladium on inert supports have also been used. Gas-phase hydrogenation of esters of adipic acid has been carried out at pressures in the range of about 1-7 MPa.

The production of 1,6-hexanediol from adipic acid hinders the prospects of utilizing hexanediol as a building block chemical for the production of large volume valuable chemicals because of the stand-alone commercial value of the feedstock, adipic acid. In support of that proposition, it is notable that the current market for adipic acid is almost 6 billion lbs/annum, but the current worldwide production of 1,6-hexanediol is only on the order of about 250M lbs/annum.

For many years there has been an interest in using renewable materials as a feedstock to replace or supplement crude oil derived basic chemicals as the feedstock for the production of intermediate and specialty chemicals. See, for example, Klass, Biomass for Renewable Energy, Fuels, and Chemicals, Academic Press, 1998, which is incorporated herein by reference. Given the steep rise in the price of oil and its price volatility, there is an ever increasing interest in shifting away from the utilization of conventional, oil-derived starting materials. Recently, processes for the production of 1,6-hexanediol from fructose via 5-hydroxymethylfurfural have been disclosed in WO2011/149339, although the disclosed processes appear to suffer from very low yields. Also disclosed therein are processes for converting 1,6-hexanediol to large volume chemicals such as caprolactam.

If processes for the production of 1,6-hexanediol from renewable feedstock at a cost less than the current cost for producing the same from oil-derived adipic acid could be commercialized, 1,6-hexanediol could become a vital building block chemical the uses for and production volume of which would expand exponentially.

U.S. Pat. No. 4,400,468 discloses a process for producing adipic acid from a renewable resource, specifically, biomass such as waste material selected from paper, wood, cornstalks and logging residue. The process involves oxidizing 1,6-hexanediol in the presence of a microorganism, such as *Gluconobacter oxydans* subsp. *oxydans*, to produce adipic acid. No examples are disclosed in this patent regarding any yields obtainable from this process.

In light of the changing environment toward utilization of cheaper, renewable feedstocks, the discovery of new, industrially scalable methods for the selective and economical production of adipic acid from 1,6-hexanediol could have extraordinary value in the near future.

SUMMARY

The present invention is directed to processes for preparing adipic acid from 1,6-hexanediol, which may be obtained from renewable materials. Generally, the process for preparing adipic acid from 1,6-hexanediol includes chemocatalytically converting 1,6-hexanediol to the adipic acid product in the presence of oxygen and a heterogeneous catalyst that may include platinum and/or gold.

In one aspect, provided is a process for preparing adipic acid product, by: reacting 1,6-hexanediol and oxygen in the presence of a catalyst that includes platinum on a zirconia or stabilized zirconia support. In some embodiments, the heterogeneous catalyst has a support, in which the outer surfaces of the support are made up of a material selected from zirconia, stabilized zirconia, zirconia-metal or -metal oxide composites, titania, stabilized titania, titania-metal or -metal oxide composites, silica and mixtures thereof. In certain embodiments, the surface area of the support is equal to or less than about 220 m²/g and the average pore diameter is at least about 5 nm. In certain embodiments, the support further includes tungsten.

In other embodiments, the heterogeneous catalyst includes a support selected from zirconia, stabilized zirconia, stabilized zirconia-metal or -metal oxide composite, titania, stabilized titania, stabilized titania-metal or -metal oxide composite, and mixtures thereof. In certain embodiments, the support is selected from stabilized zirconia, stabilized titania, and mixtures thereof, and the support contains tungsten. In certain embodiments, the tungsten is present in an amount ranging from about 1 wt % to about 15 wt % of the total weight of the support. In yet other embodiments, the support has a surface equal to or less than about 220 m²/g and an average pore diameter of at least about 5 nm. In one embodiment, the support has a surface equal to or less than about 100 m²/g and an average pore diameter of at least about 10 nm.

In some embodiments, reacting the 1,6-hexanediol with oxygen in the presence of the heterogeneous catalyst includes: a) combining the 1,6-hexanediol and the heterogeneous catalyst, and optionally a solvent; and b) contacting the combined 1,6-hexanediol and heterogeneous catalyst, and optionally the solvent, with oxygen. In certain embodiments, reacting the 1,6-hexanediol with oxygen in the presence of the heterogeneous catalyst, and optionally a solvent includes: a) combining the 1,6-hexanediol and the heterogeneous catalyst, and optionally a solvent, at a temperature equal to or less than about 120° C.; and b) contacting with oxygen the combined 1,6-hexanediol and heterogeneous catalyst, and optionally the solvent.

In other embodiments, reacting the 1,6-hexanediol with oxygen in the presence of the heterogeneous catalyst includes: a) combining the 1,6-hexanediol and a solvent; b) contacting the combined 1,6-hexanediol and solvent with a heterogeneous catalyst; and c) contacting the combined 1,6-hexanediol, solvent, and heterogeneous catalyst with oxygen. In certain embodiments, the solvent is selected from water, alcohols, ethers, and mixtures thereof.

In yet other embodiments, reacting the 1,6-hexanediol with oxygen in the presence of the heterogeneous catalyst and water includes: a) contacting the 1,6-hexanediol with water; b) contacting the 1,6-hexanediol and water with the heterogeneous catalyst; and c) contacting the combined 1,6-hexanediol, water, and heterogeneous catalyst with oxygen.

In some embodiments, the 1,6-hexanediol is derived from a carbohydrate source. In some embodiments, the reaction is conducted under a partial pressure of oxygen ranging from about 50 psi to about 2000 psi. In certain embodiments, the partial pressure of oxygen ranges from about 50 psig to about 1000 psig. In one embodiment, the partial pressure of oxygen ranges from about 50 psig to about 700 psig. In other embodiments, the reacting the 1,6-hexanediol with oxygen in the presence of a heterogeneous catalyst is carried out at a temperature ranging from about 100° C. to about 180° C. In certain embodiments, the reacting the 1,6-hexanediol with oxygen in the presence of a heterogeneous catalyst is carried out at a temperature ranging from about 135° C. to about 165° C. In some embodiments, the adipic acid product is produced in at least about 80% yield from the 1,6-hexanediol. In one embodiment, the adipic acid product is produced in at least about 90% yield from the 1,6-hexanediol.

In some embodiments, the catalyst further includes palladium. In other embodiments, gold is present in an amount up to about 4 wt % of the total catalyst weight. In yet other embodiments, platinum is present in an amount up to about 4 wt % of the total catalyst weight. In certain embodiments, the catalyst includes gold and platinum, and the gold and platinum are present in an amount, in sum, up to about 4 wt % of the total catalyst weight.

Provided is also a catalyst that includes at least one metal selected from gold and platinum, in which the at least one metal is on a support, in which at least the outer surfaces of the support are made up of zirconia or stabilized zirconia, wherein the surface area of the support is equal to or less than about 100 m²/g and the average pore diameter is at least about 10 nm and wherein the zirconia or stabilized zirconia includes tungsten in an amount ranging from about 1 wt % to about 15 wt % of the total weight of the support. In some embodiments, the outer surfaces consist essentially of stabilized zirconia. In one embodiment, the catalyst consists essentially of platinum on such support. In another embodiment, the catalyst consists essentially of platinum and gold on such support. In other embodiments, the catalyst further includes palladium. In one embodiment, the at least one metal is present, in sum, in an amount up to about 4 wt % of the total weight of the catalyst.

DETAILED DESCRIPTION

The following description sets forth exemplary methods, parameters and the like. It should be recognized, however, that such description is not intended as a limitation on the scope of the present invention.

Provided herein are processes for the chemocatalytic conversion of 1,6-hexanediol to adipic acid. Generally, the processes for producing adipic acid includes chemocatalytically converting 1,6-hexanediol to an adipic acid product in the presence of oxygen and a heterogeneous catalyst comprising platinum and/or gold.

Adipic acid prepared in accordance with the disclosed processes may be converted to various other industrially significant chemicals (e.g., adiponitrile, hexamethylenediamine, caprolactam, caprolactone, adipate esters, polyamides such as nylons, and polyesters) according to processes known in the art.

1,6-Hexanediol may be obtained from various commercial suppliers known to those of ordinary skill in the art, produced by employing commercial processes hereinabove described, or may be obtained from processing renewable resources such as corn grain (maize), sugar cane, sugar beet, wheat, potato, cassava and rice as well as alternative sources such as energy crops, plant biomass, agricultural wastes, forestry residues, sugar processing residues and plant-derived household wastes to produce fructose which can be converted to 1,6-hexanediol by, for example, the processes disclosed in WO2011/149339.

Applicants have discovered that 1,6-hexanediol may be converted to adipic acid in a single step according to the following overall reaction scheme:

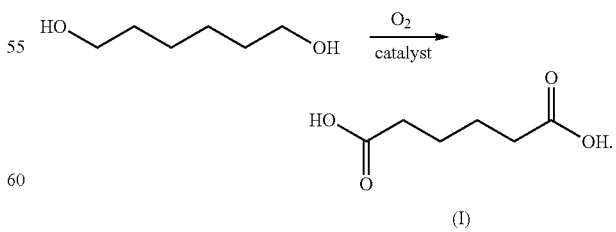

(I)

Catalysts suitable for the oxidation reaction (oxidation catalysts) are particular supported heterogeneous catalysts that include one or more metals on at least the external surfaces (the "exposed surfaces") of a support, which metals are selected from platinum (Pt), gold (Au), and a combination thereof. In general, the metals may be present in various forms. In some embodiments, the metals may be present in elemental, metal oxide, metal hydroxides, metal ions, or alloys. In various preferred embodiments, the metals are present in elemental form and/or as alloy or intermetallic compound. Typically, the total weight percent of metal (to the total weight of the finished catalyst) is from about 0.1 wt % to about 10 wt %, or from 0.2 wt % to 10 wt %, or from about 0.2 wt % to about 8 wt %, or from about 0.2 wt % to about 5 wt %, of the total weight of the catalyst. In more preferred embodiments, the total weight of metal is equal to or less than about 4 wt %.

As described above, the catalyst include at least a first metal (M1) selected from the above mentioned group. One or more other metals (M2) may be present including other metals within the above described group. The metals are deposited onto solid phase supports to produce the heterogeneous catalyst of the present invention. In many preferred embodiments, M1 is Pt or Au and M2 is selected from the remaining metals of the above mentioned group, palladium, or combinations thereof. The M1:M2 molar ratio may vary. Generally, the molar ratio of M1:M2 is in the range of from about 20:1 to about 1:1. More typically, the ratio is in the range of from about 15:1 to about 1:1, and still more typically in the range of from about 10:1 to about 1:1. When M1 is Pt, the ratio of Pt:M2 is in the range of from about 20:1 to about 1:1 and preferably from about 10:1 to about 1:1. When M1 is Au, the ratio of Au:M2 is in the range of from about 20:1 to about 1:1 and preferably from about 10:1 to about 1:1.

The catalysts of the present invention are heterogeneous, solid-phase, supported catalysts. Catalyst supports useful in combination with the above-described metals to form the heterogeneous, supported catalysts of the present invention can be any of a variety of known supports such as silicas, carbon, zirconias, titanias, aluminas, metal oxide-composites and mixtures thereof. Supports which have been surprisingly effective in the conversion of 1,6-hexanediol to adipic acid are silicas ($SiO_2$), zirconias ($ZrO_2$), and titanias ($TiO_2$), especially zirconias. When referring to support materials such as, for example, zirconias or titanias, it should be understood that the term includes stabilized (doped) product. Thus, the term "zirconia(s)" or "titania(s)" as used herein includes oxides and up to about 5 wt % of other materials, more typically less than about 2 wt % of other materials, not intentionally added to perform a specific function. Typically, these "trace" materials include, for example, hafnium, silica and/or titania (the latter in the case of zirconia). Zirconia can exist in one or more crystalline phases, for example, as essentially monoclinic, essentially tetragonal, monoclinic with a small fraction of tetragonal, or tetragonal with a small fraction of monoclinic. Stabilized zirconia (also referred as "doped" zirconia) is zirconia in combination with one or more metal or metal oxides intentionally added to stabilize one or more of the phases of which the zirconia may exist, and typically the addition(s) is(are) present to stabilize the tetragonal phase of zirconia. Dopants used to stabilize zirconia are present in the range of between about 1 wt % and about 40 wt % of the total weight of the stabilized material, but more typically are less than about 20 wt % of the total weight of the stabilized material. Typical dopants/stabilizers include silica, titania, lanthana, yttria, ceria, tungsten, molybdenum, lanthanides, and mixtures thereof. Preferred dopants are tungsten, molybdenum and silica. Zirconia (or stabilized-zirconia)-metal oxide composites are shell and core composites wherein the zirconia (or stabilized zirconia) forms the shell of the support and another metal oxide (or different zirconia or stabilized zirconia) forms the core of the support. Useful core materials, in addition to zirconia or stabilized zirconia, include silicas or silicates, titanias and aluminas. Those of ordinary skill in the art are readily capable of producing useful composite catalyst supports. Titania, like zirconia, exists in more than one phase: as essentially rutile, essentially anatase, rutile with a fraction of anatase, or anatase with a fraction of rutile.

The catalysts of the present invention are particularly effective in part because the surface area of the supports thereof are equal to or less than about 220 $m^2/g$, and especially effective when the surface area is equal to or less than about 100 $m^2/g$. Further, controlling the average pore diameters of the support also advantageously, and unexpectedly, benefits the performance of the catalysts of the present invention; to that end, the average pore diameters of the supports of the present invention are in the range of at least about 5 nanometer (nm) to about 70 nanometer (nm), preferably at least about 10 nm, and exhibit a monomodal or multimodal pore size distribution. Average pore diameters are determined in accordance with the procedures described in E. P. Barrett, L. G. Joyner, P. P. Halenda, J. Am. Chem. Soc. 1951, 73, 373-380, and ASTM D4222-03(2008) Standard Test Method for Determination of Nitrogen Adsorption and Desorption Isotherms of Catalysts and Catalyst Carriers by Static Volumetric Measurements. Surface area is determined in accordance with the methods described in S. Brunauer, P. H. Emmett, E. Teller, J. Am. Chem. Soc. 1938, 60, 309-331, and ASTM D3663-03(2008) Standard Test Method for Surface Area of Catalysts and Catalyst Carriers.

The overall shape of the catalyst support is not believed to be critical. The catalysts can be in the form of, for example, spheres, beads, cylinders, lobed shapes (for example, bi-, tri-, star-), holed (for example, rings, cored beads, spheres, cylinders, or lobe shapes), and the metal distribution on the surface of the support can be uniform or non-uniform. Typically, the metal is distributed such that it forms a metal-impregnated outer shell having a thickness in the range of about 30 μm to about 150 μm, and more typically the thickness of the metal-impregnated outer shell is equal to or less than about 100 μm.

The catalysts of the present invention may be produced by deposition procedures known in the art including, but not limited to, incipient wetness, ion-exchange and deposition-precipitation and absorption from excess solution (volume higher than ion exchange or incipient wetness), physical vapor deposition, chemical vapor deposition, solution coating or wash coating. In various embodiments, a uniform dispersion can be effected by forming a heterogeneous slurry or suspension of the support in combination with solubilized metal complexes. In certain embodiments, the supports may be initially dispersed in a liquid such as water; thereafter, in such embodiments, the solubilized metal complexes may be added to the slurry containing the support. The heterogeneous mixture of solid and liquids can then be stirred, mixed and/or shaken or fluidized to enhance the uniformity of dispersion of the catalyst components which, in turn, enables the more uniform deposition of metals on the surface of the support upon removal of the liquids and undertaking additional treatments as may be needed to produce the catalyst (and more fully described hereinafter). The opposite order of addition (i.e., adding the support to the metal solution) is also possible.

The platinum is typically added to the support as a solution of a soluble precursor or as a colloid. Platinum-containing compounds useful in the present invention include nitrogen-containing compounds and chloride-containing compounds. Suitable platinum-containing compounds include, for example, platinum (II) dinitrate, platinum (IV) nitrate, platinum oxynitrate, tetraamineplatinum (II) nitrate, tetraamineplatinum (II) hydrogenphosphate, tetraamineplatinum (II) hydrogencarbonate, tetraamineplatinum (II) hydroxide, ethanolaminehexahydroxyplatinate (IV) complex, alkali metal-hexahydroxyplatinate (IV) complexes, tetraalkylammoniumhexahydroxyplatinate (IV) complexes, platinum (II) acetylacetanoate, platinum (II) oxalate, diamine-platinum (II) nitrite, potassium-platinum (II) nitrite, and potassium platinum (II) oxalate. Suitable chloride-containing compounds include, for example, platinum (IV) chloride, platinum (II) chloride, ethanolamineplatinum (IV) chloride complex, potassium or sodium or ammonium tetrachloroplatinate (II), tetraamine platinum (II) chloride and diamine Pt(II) dichloride. Some preferred compounds include, for example, platinum (II) dinitrate, platinum (IV) chloride, and potassium or sodium tetrachloroplatinate (II). The platinum precursor solutions can optionally be stabilized by mineral acids, ammonia, alkali metal solutions such as NaOH, alkali metal salts such as NaCl, ethanolamine or carboxylic acids such as glycolic acid or oxalic acid.

If gold is present, it is typically added to the support as a solubilized constituent to enable the formation of a uniform suspension. In certain embodiments, a base is then added to the suspension in order to create an insoluble gold complex which can be more uniformly deposited onto the support. For example, in various embodiments, the solubilized gold constituent is provided to the support as, for example, $HAuCl_4$. Upon creation of a well dispersed, heterogeneous mixture, a base is added to the mixture to form an insoluble gold complex which then deposits on the surface of the support. Although any base which can effect the formation of an insoluble gold complex is useable, in various embodiments nitrogen-containing bases such as ammonia or urea are employed. In some embodiments, it may be desirable, though not required, to collect the support on which has been deposited the insoluble gold complex prior to adding the platinum-containing constituent, which collection can readily be accomplished by any of a variety of means known in the art such as, for example, centrifugation. The collected solids may optionally be washed and then may be heated to dry. Alternatively, gold may be added to the support as a solution of a soluble precursor or as a colloid. Gold-containing compounds useful in the present invention include tetramethylamine aurate, gold (III) nitrate, cesium aurate, potassium aurate, sodium aurate, gold (III) chloride, tetrachloroauric acid and sodium tetrachloroaurate.

If palladium is present, it is typically added to the support as a solution of a soluble precursor or as a colloid. Palladium-containing compounds useful in the present invention include, for example, palladium nitrate, diaminedichloropalladium (II), ammonium hexachloropalladate (IV), ammonium tetrachloropalladate (II), palladium (II) chloride, potassium hexachloropalladate (IV), sodium tetrachloropalladate (II) and tetraaminepalladium (II) nitrate.

When two or more metals are deposited on the same support, they may be deposited sequentially or simultaneously. In various embodiments, following metal deposition, the catalyst is dried at a temperature in the range of about 20° C. to about 120° C. for a period of time ranging from at least about 1 hour to about 24 hours. In these and other embodiments, the catalyst is dried under sub-atmospheric pressure conditions. In various embodiments, the catalyst is reduced after drying (e.g., by flowing 5% $H_2$ in $N_2$ at a temperature of at least about 200° C. for a period of time e.g., at least about 3 hours). Preferably, drying is conducted at a temperature in the range of about 40° C. to about 90° C. and more preferably at a temperature at least about 60° C. Drying of the catalyst precursor can be conducted, for example, on a band dryer, in a direct fired rotary oven, or in an indirect fired rotary oven. When using physical coating for the metal deposition, drying may be done simultaneously with the coating step in the coating chamber. After deposition of the metal precursors an auxiliary chemical agent (e.g., precipitation agent) may be added, either before and/or after drying, to convert the precursors into more easily reducible or thermally decomposable forms.

After drying, the support having the precursor compound deposited thereon and, possibly, therein is typically subjected to at least one thermal treatment, under oxidative (calcination), inert (nitrogen, argon) and/or reductive (gas phase or liquid phase reductants) conditions, as is necessary for the metals of the catalyst, in order to convert at least the platinum to Pt(0). In some embodiments, the catalysts may be calcined and then the metal may be further reduced in-situ (i.e., in the reactor). In the case of platinum, the platinum of the compound is reducible to Pt(0) upon thermal treatment regardless of whether the atmosphere is oxidizing, inert or reducing. Thus, thermal treatment(s) may, for example, be conducted in air. Preferably, the substantial decomposition of the Pt precursor occurs during calcination and at least a portion of the platinum is converted to Pt(0). In the case of gold, the gold of the compound is reducible to Au(0) upon thermal treatment regardless of whether the atmosphere is oxidizing, inert or reducing. Thus, thermal treatment(s) may, for example, be conducted in air. Preferably, the substantial decomposition of the Au precursor occurs during calcination and at least a portion of the platinum is converted to Au(0). When palladium is present, thermal treatment under reductive conditions are necessary to convert a least a portion of the palladium to Pd(0). Therefore, in various embodiments, the thermal treatment(s) is (are) conducted under a hydrogen gas containing atmosphere; alternatively, for example, a liquid reducing agent may be employed to reduce the platinum compound to platinum(0) on the support: for example, hydrazine, formaldehyde, formic acid, sodium formate or sodium hypophosphite may be employed to effect the requisite reduction.

The temperature(s) at which the calcination treatment(s) is (are) conducted generally range from about 150° C. to about 600° C. More typically, the temperature(s) of the thermal treatment(s) range from about 200° C. to about 550° C. The thermal treatment is typically conducted for a period of time ranging from about 1 hour to about 16 hours. More typically, the treatment is conducted for a period of time ranging from about 2 hours to about 12 hours. For example, at a thermal treatment temperature of about 350° C., the time of the treatment at temperature is in the range of about 2 hours to about 6 hours.

When a thermal treatment is conducted under a hydrogen gas-containing atmosphere (a reducing atmosphere), the thermal treatment under such gas phase reductive conditions is generally conducted at a temperature range from about 100° C. to about 500° C. When the thermal treatment is conducted in the presence of a liquid phase reducing agent, the thermal treatment under liquid phase reductive conditions is conducted at a temperature range from about 20° C. to about 95° C. In various embodiments, a thermal treatment under reducing conditions can be conducted subsequent to a calcination treatment.

Optionally, a washing step can be employed after a thermal treatment to remove non-decomposable counterion(s) of the metal precursor compounds, such as Na, K, Cl. Typical wash solutions can include, for example, water, alcohols, polyols, carboxylic acids, or mixtures thereof. The wash solution may optionally contain a chemical reagent that will complex the counterion(s).

In some embodiments, a third metal (M3) may be added to produce a (Pt or Au)/(Pt, Au or Pd)/M3 catalyst wherein the M3 metal is not the M1 or M2 metal. In yet other embodiments, a fourth metal (M4) may be added to produce a (Pt or Au)/(Pt, Au or Pd)/M3/M4 catalyst wherein the M4 metal is not any of platinum, gold or palladium and also not the same metal as the M3 metal. Subject to the preceding limitations, the M3 metal and M4 metal may each be selected from group of palladium, ruthenium, iridium, gold, molybdenum, tungsten, niobium, tantalum, rhenium, and osmium. More preferably, the M3 metal is selected from palladium, molybdenum and tungsten and the M4 metal is molybdenum or tungsten.

The oxygen can be supplied to the reaction as air, oxygen-enriched air, oxygen alone, or oxygen with other constituents substantially inert to the reaction in the presence of a heterogeneous catalyst and 1,6-hexanediol. The partial pressure of oxygen is typically at least about 50 pounds per square inch (psig). In various embodiments, the partial pressure of oxygen is up to about 2000 psig. More typically, the partial pressure of oxygen is in the range of from about 50 psig to about 1000 psig. In many preferred embodiments, the partial pressure of oxygen is in the range of from about 50 psig to about 700 psig.

Generally, the temperature of the reaction mixtures, regardless of the order of addition of reaction constituents, or the conduct of the overall conversion in one or more reactors or reactor zones, is at least about room temperature. Typically, the temperature of the reaction mixture(s) is(are) maintained in the range of from about room temperature (about 20° C.) to about 300° C., and more typically in the range of from about 100° C. to about 180° C. In various preferred embodiments, the temperature(s) is (are) maintained in the range of from about 135° C. to about 165° C.

The oxidation reaction can also be conducted in the presence of a solvent. Solvents suitable for use in conjunction with the oxidation reaction may include, for example, water, alcohols, esters, ethers, ketones, or mixtures thereof. In various embodiments, the preferred solvent is water.

The order in which the 1,6-hexanediol, solvent (if employed), oxygen, and catalyst are combined to carry out the conversion of the 1,6-hexanediol to an adipic acid product may vary. In various embodiments, reaction constituents can be added initially at room temperature. In other embodiments, reaction constituents can be added at elevated temperatures such as, for example, up to about 100° C.

In some embodiments, the 1,6-hexanediol, the catalyst and solvent can be first combined, before addition of oxygen. The resulting reaction mixture may then be heated, subjected to appropriate oxygen partial pressure and other process conditions such as, for example, flow rate of the combined reaction constituents to the reaction zone(s).

In other embodiments, the 1,6-hexanediol can be contacted with solvent and oxygen before contact with catalyst. In some variations, the 1,6-hexanediol may be contacted with a solvent in the absence of the catalyst and, optionally, preheated before contact with the catalyst.

In yet other embodiments, the heterogeneous catalyst may first be contacted with oxygen, before addition of the 1,6-hexanediol and a solvent.

In still other embodiments, the heterogeneous catalyst and solvent can be first combined, before addition of the 1,6-hexanediol and the oxygen.

In other embodiments, the 1,6-hexanediol can initially be combined only with water, and then the contacted with other/additional solvent, oxygen, and catalyst. In variations hereof, the 1,6-hexanediol can initially be combined with water and thereafter oxygen, another/additional solvent, and thereafter the catalyst may be added.

In general, the oxidation reactions can be conducted in a batch, semi-batch, or continuous reactor design using fixed bed reactors, trickle bed reactors, bubble up reactors, slurry phase reactors, moving bed reactors, or any other design that allows for heterogeneous catalytic reactions. Examples of reactors are described in *Chemical Process Equipment—Selection and Design*, Couper et al., Elsevier 1990, which is incorporated herein by reference. Again, it should be understood that the 1,6-hexanediol, oxygen, any solvent, and the catalyst may be introduced into a suitable reactor separately or in various combinations, as generally described hereinabove.

The chemocatalytic conversion of 1,6-hexanediol to adipic acid may yield a mixture of products. In several embodiments, at least 50%, at least 60%, or at least 70% of the product mixture is adipic acid. In several embodiments, the production of adipic acid is at least about 60%, at least about 70%, at least about 80%, or at least about 90%. With platinum on zirconia catalyst, adipic acid yields in excess of 90% have been achieved.

The adipic acid may be recovered from any remaining other products of the reaction mixture by one or more conventional methods known in the art including, for example, solvent extraction, crystallization, or evaporative processes, the preferred method being crystallization.

When introducing elements of the present invention or the preferred embodiments(s) thereof, the articles "a", "an" are intended to be the singular unless the context admits otherwise and "the" and "said" are intended to mean that there are one or more of the elements. The terms "comprising", "including" and "having" are not intended to be inclusive and use of such terms mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description shall be interpreted as illustrative and not in a limiting sense.

Having described the invention in detail, it will be apparent that modifications and variations are possible without departing from the scope of the invention defined in the appended claims.

EXAMPLES

The following non-limiting examples are provided to further illustrate the present invention.

Example 1: 1,6-Hexanediol to Adipic Acid Using Au, Au—Pd & Au—Pt Catalysts

Approximately 25 µl of aqueous solutions of $HAuCl_4$ (containing 28.6 wt % gold) were added to suspensions containing 600 mg supports: Silica Cariact Q-10 (Fuji Silysia); Titania ST 31119 (St. Gobain); and Zirconia (produced by St. Gobain from Zirconia XZO 1247—a zirconium hydroxide—from MEL Chemicals) in deionized water (35 ml) while shaking. The suspensions were shaken at room temperature for 5 min. 1.92 ml of aqueous solutions of NH$_4$OH (15.85 M) was added to the above-mentioned suspensions and the resulting suspensions were shaken at room temperature for 2 hours. The resulting suspensions were then centrifuged and colorless supernatants were decanted. After residual liquid was removed using filter paper, the yellow-orange solids were dried in a 60° C. oven overnight under a dry air purge.

The above ca. 2 wt % Au-containing supports were each split into thirds. Suitably concentrated aqueous solutions of Pd(NO$_3$)$_2$ or Pt(NO$_3$)$_2$ were added to about 200 mg of each Au-containing support and agitated to impregnate the supports. The impregnated supports were dried in an oven at 60° C. overnight under a dry air purge. The dried, impregnated supports were heated at 200° C. under forming gas (5% H$_2$ and 95% N$_2$) atmosphere for 3 hours with 5° C./min temperature ramp rate. The final catalysts were composed of ca. 2 wt % Au; 2 wt % Au and 0.1 wt % Pd; or 2 wt % Au and 0.2 wt % Pt on each support: silica, titania, and zirconia.

Oxidation of 1,6-hexanediol was undertaken using the following testing protocol. Each of the final catalyst (ca. 10 mg) was weighed in a glass vial insert followed by addition of an aqueous 1,6-hexanediol solution (200 μl of 0.1 M). The glass vial insert containing the catalyst and reaction substrate was loaded into a reactor and the reactor was closed. The atmosphere in the reactor was replaced with oxygen and pressurized to 100 psig at room temperature, and further pressurized by nitrogen to 500 psig at room temperature. The reactor was heated to 140° C. or 160° C. and maintained at temperature for 120 or 60 minutes, respectively, while vials were shaken. After the allotted time passed, shaking was stopped and reactor was cooled to 40° C. Pressure in the reactor was then slowly released. The glass vial insert was removed from the reactor and centrifuged. The clear solution was diluted with methanol and analyzed by gas chromatography with flame ionization detection. The results are reported in Table 1.

TABLE 1

| Entry | Run Temperature (° C.) | Metal | Support | 1.6-Hexanediol Conversion (%) | Adipic Acid Yield (%) |
|---|---|---|---|---|---|
| 1 | 140 | Pt— | Silica Caraict | 100 | 77 |
| 2 | 140 | Au | Titania ST | 100 | 75 |
| 3 | 140 | Pt— | Titania ST | 100 | 89 |
| 4 | 140 | Au | Zirconia | 100 | 94 |
| 5 | 140 | Pd— | Zirconia | 100 | 88 |
| 6 | 140 | Pt— | Zirconia | 100 | 78 |
| 7 | 160 | Au | Silica Caraict | 100 | 83 |
| 8 | 160 | Pd— | Titania ST | 100 | 86 |
| 9 | 160 | Au | Zirconia | 100 | 87 |
| 10 | 160 | Pd— | Zirconia | 100 | 85 |
| 11 | 160 | Pt— | Zirconia | 100 | 76 |

Example 2: 1,6-Hexanediol to Adipic Acid Using Pt Catalysts

Zirconia Z-2087 (Daiichi Kigenso Kagaku Kogyo) support was dried in an oven at 60° C. overnight under a dry air purge. The sample was calcined at 650° C. under air atmosphere for 3 hours with 5° C./min temperature ramp rate. A suitably concentrated aqueous solution of Pt(NO$_3$)$_2$ was added to 200 mg of support and agitated to impregnate the supports. The sample was dried in an oven at 60° C. overnight under a dry air purge. The samples were reduced at 350° C. under forming gas (5% H$_2$ and 95% N$_2$) atmosphere for 3 hours with 5° C./min temperature ramp rate. The final catalyst was composed of ca. 3.9 wt % Pt.

Oxidation of 1,6-hexanediol was undertaken using the following testing protocol. Catalyst (ca. 10 mg) was weighed into a glass vial insert followed by addition of an aqueous 1,6-hexanediol solution (200 μl of 0.1 M). The glass vial insert was loaded into a reactor and the reactor was closed. The atmosphere in the reactor was replaced with oxygen and pressurized to 100 psig at room temperature, and further pressurized by nitrogen to 500 psig at room temperature. The reactor was heated to 140° C. or 160° C. and maintained at temperature for 120 or 60 minutes, respectively, while the vials were shaken. After the allotted time passed, shaking was stopped and reactor was cooled to 40° C. Pressure in the reactor was then slowly released. The glass vial insert was removed from the reactor and centrifuged. The clear solution was diluted with methanol and analyzed by gas chromatography with flame ionization detection. The results are reported in Table 2.

TABLE 2

| Entry | Run Temperature (° C.) | Metal | Support | 1.6-Hexanediol Conversion (%) | Adipic Acid Yield (%) |
|---|---|---|---|---|---|
| 1 | 140 | Pt | Zirconia Z- | 100 | >99 |
| 2 | 160 | Pt | Zirconia Z- | 100 | 93 |

We claim:

1. A process for preparing adipic acid, the process comprising reacting 1,6-hexanediol and oxygen in the presence of a catalyst comprising platinum on a support comprising zirconia or stabilized zirconia thereby producing a reaction mixture comprising adipic acid, wherein the catalyst does not include gold.

2. The process of claim 1, wherein the surface area of the support is equal to or less than about 220 m$^2$/g.

3. The process of claim 2, wherein the surface area of the support is equal to or less than about 100 m$^2$/g.

4. The process of claim 2, wherein the average pore diameter of the support is in the range of at least about 5 nanometer to about 70 nanometer.

5. The process of claim 4, wherein the average pore diameter of the support is at least about 10 nm.

6. The process of claim 1, wherein the support further comprises tungsten.

7. The process of claim 6, wherein the tungsten is present in an amount ranging from about 1 wt % to about 15 wt % of the total weight of the support.

8. The process of claim 1, wherein the reacting the 1,6-hexanediol with oxygen in the presence of a heterogeneous catalyst is carried out at a temperature in the range of from about 100° C. to about 180° C.

9. The process of claim 8, wherein the reacting the 1,6-hexanediol with oxygen in the presence of a heterogeneous catalyst is carried out at a temperature in the range of from about 135° C. to about 165° C.

10. The process of claim 1, wherein the reaction is conducted under a partial pressure of oxygen in the range of from about 50 psig to about 2000 psig.

11. The process of claim 10, wherein the reaction is conducted under a partial pressure of oxygen in the range of from about 50 psig to about 1000 psig.

12. The process of claim 11, wherein the reaction is conducted under a partial pressure of oxygen in the range of from about 50 psig to about 750 psig.

13. The process of claim 1, wherein the reaction is conducted in the presence of a solvent.

14. The process of claim 13, wherein the solvent comprises a solvent selected from the group consisting of water, alcohols, esters, ethers, ketones, and mixtures thereof.

15. The process of claim 14, wherein the solvent is water.

16. The process of claim 1, wherein the adipic acid is produced at a yield of at least about 60%.

17. The process of claim 16, wherein the adipic acid is produced at a yield of at least about 70%.

18. The process of claim 17, wherein the adipic acid is produced at a yield of at least about 80%.

19. The process of claim 18, wherein the adipic acid is produced at a yield of at least about 90%.

20. The process of claim 1, further comprising recovering the adipic acid from the reaction mixture.

21. The process of claim 2, wherein the reacting the 1,6-hexanediol with oxygen in the presence of a heterogeneous catalyst is carried out at a temperature in the range of from about 100° C. to about 180° C.

22. The process of claim 12, wherein the reacting the 1,6-hexanediol with oxygen in the presence of a heterogeneous catalyst is carried out at a temperature in the range of from about 100° C. to about 180° C.

* * * * *